United States Patent [19]

Partridge et al.

[11] Patent Number: 5,339,155
[45] Date of Patent: Aug. 16, 1994

[54] OPTICAL WAVELENGTH MODULATED LONG-PATH GAS MONITORING APPARATUS

[75] Inventors: Roger H. Partridge, Leatherhead; Robert H. Bradsell, Hampton; Peter T. Woods, Walton-on-Thames, all of United Kingdom

[73] Assignee: Secretary of State for Trade Industry, London, England

[21] Appl. No.: 40,565

[22] Filed: Mar. 31, 1993

Related U.S. Application Data

[63] Continuation of Ser. No. 731,745, Jul. 16, 1991, abandoned.

[30] Foreign Application Priority Data

Jul. 18, 1990 [GB] United Kingdom ............. 9015800

[51] Int. Cl.5 .................... G01N 21/31; G01N 21/35
[52] U.S. Cl. ................. 356/419; 250/339.06; 356/437
[58] Field of Search ............. 356/419, 437; 250/339

[56] References Cited

U.S. PATENT DOCUMENTS

| 4,090,792 | 5/1978 | Bunge | 356/419 X |
| 5,015,099 | 5/1991 | Nagai et al. | 356/437 |
| 5,076,699 | 12/1991 | Ryan et al. | 356/437 |

FOREIGN PATENT DOCUMENTS

| 61-48736 | 3/1986 | Japan | 356/437 |
| WO89/03028 | 4/1989 | World Int. Prop. O. | 356/437 |

*Primary Examiner*—Vincent P. McGraw
*Attorney, Agent, or Firm*—Joseph S. Iandiorio

[57] ABSTRACT

Optical long-path gas monitoring apparatus (2) comprising means (4) for providing a radiation beam, a modulator (10) for modulating the wavelength of the radiation beam such as to produce amplitude modulation of the beam in the presence of the gas being monitored, a radiation detector (12) for conversion of the radiation beam into an electrical signal, and a signal processor (PSD 1, PSD 2) for demodulating the electrical signal to provide a signal dependent upon the gas.

10 Claims, 5 Drawing Sheets

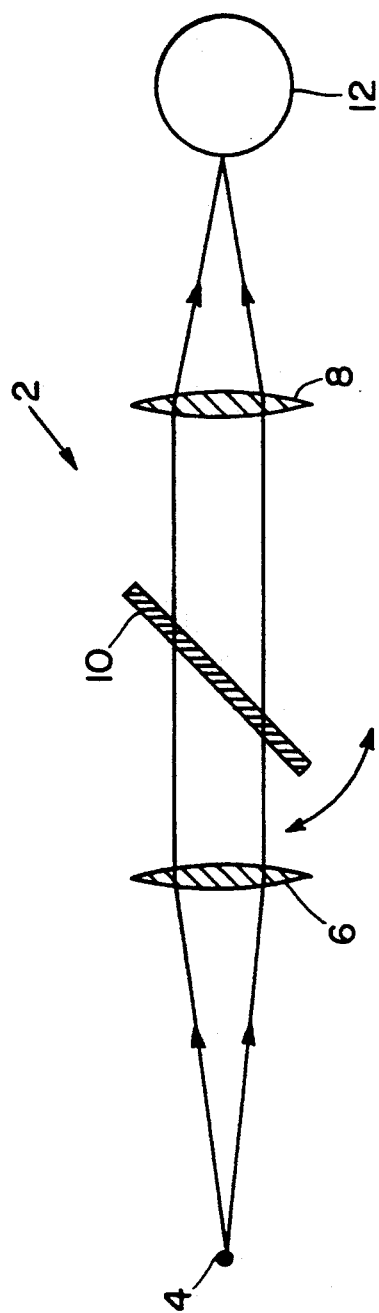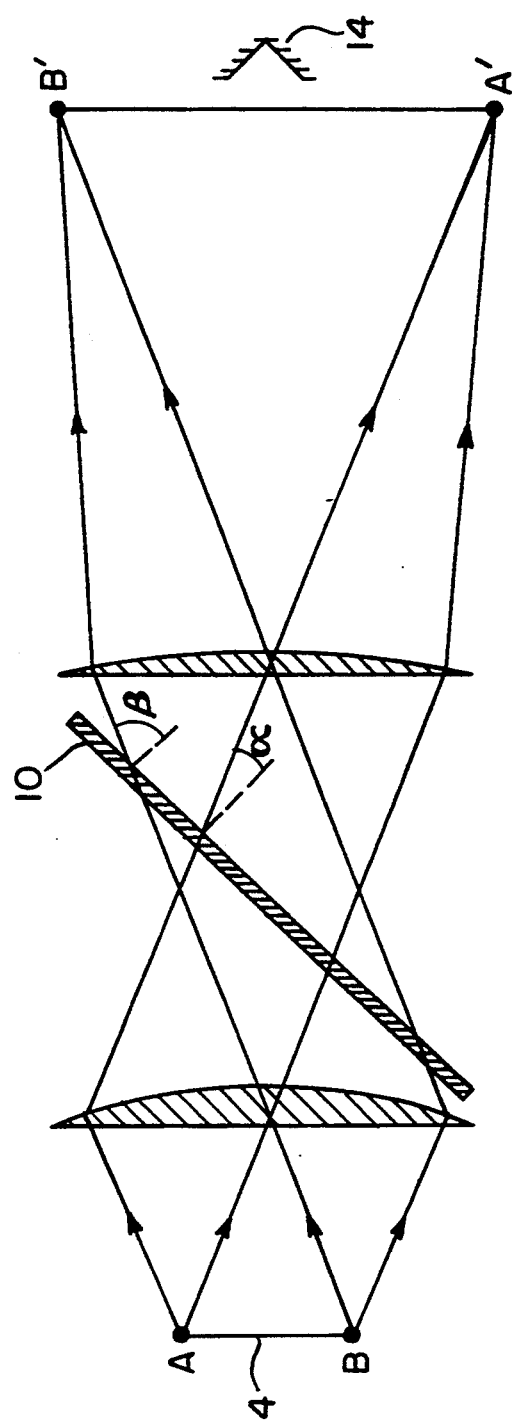
Fig. 2
Fig. 3

OPTICAL WAVELENGTH MODULATED LONG-PATH GAS MONITORING APPARATUS

This is a continuation of application Ser. No. 07/731,745, filed Jul. 16, 1991, now abandoned.

This invention relates to optical long-path gas monitoring apparatus.

Various types of optical gas monitoring apparatus exist. Most of these known types of apparatus are what are known as point monitors since they measure gas at a single very localised region in space. These point monitors generally use a twin wavelength differential absorption principle in which two optical beams of different wavelengths are employed, one optical beam being such that it can be absorbed by the gas to be measured, and the other optical beam being such that it is only slightly absorbed by the gas to be measured. If the gas to be measured is present, then one beam is absorbed and the other is not, and the amount of the gas to be measured can be inferred from the difference between the two beam intensities. More than two wavelengths can be used if it is necessary to measure, or discriminate against, more than one gas.

A variation of the twin wavelength differential absorption principle is known as a gas correlation technique. With the gas correlation technique, a cell containing a sample of the gas that is to be measured is placed in one of the two beams, to act as an optical filter that exactly matches the spectrum of the target gas. The intensity of this beam is compared with that of the other beam which does not have such a gas cell.

Another type of known optical gas monitoring apparatus uses a monochromator to measure the absorption spectrum of a chosen atmospheric path, and a computer to recognise the absorption spectra of individual gases within the overall spectrum.

A few known types of optical gas monitoring apparatus operate on a different detection principle to those mentioned above, and this different detection principle is known as the principle of wavelength modulation. The present invention also operates on the principle of wavelength modulation.

It is an aim of the present invention to provide optical gas monitoring apparatus which is able to operate over a long path so that, for example, the optical gas monitoring apparatus may be used to detect a variety of gases along a path between a means for providing a radiation beam and a mirror situated up to several hundred meters away. The radiation beam may be an ultra violet, visible, or infrared radiation beam. Such a long path optical gas monitoring apparatus is much more suitable than a conventional single point monitor for the measurement of large clouds of gas from, for example, leakages in pipelines, storage containers and general industrial plants.

Accordingly, the present invention provides optical long-path gas monitoring apparatus comprising radiation source means for providing a radiation beam having a broad range of wavelengths, wavelength modulation means for modulating the radiation beam at a wavelength modulation frequency over all of the wavelengths between two limits appropriate for the gas being monitored in order to produce amplitude modulation of the radiation beam in the presence of the gas being monitored, amplitude modulations means for modulating the radiation beam at a frequency different from that of the wavelength modulation frequency, radiation detector means for converting the radiation into an electrical signal, and signal processing means comprising two phase sensitive detectors to demodulate the amplitude modulated and phase modulated signals respectively to provide, upon ratioing the outputs of the phase sensitive detectors, a signal dependent upon the gas being monitored, the optical long-path gas monitoring apparatus being such that the amplitude modulation means is positioned in front of the radiation source means and in the path of the radiation beam emitted from the radiation source means into the atmosphere, and the wavelength modulation means is positioned in front of the radiation detector means such that it will be traversed by the radiation beam after the radiation beam has traversed a selected portion of the atmosphere, and the optical long-path gas monitoring apparatus being such as to include an electronic switch which is controlled by the amplitude modulation means and whose purpose is to provide two different signals at times when the amplitude modulation means is open and closed respectively, which signals when subtracted one from the other remove spurious signals in the wavelength modulation channel due to external stray radiation beam is preferably used to detect a gas to be monitored by setting the wavelength to modulate across an edge of an absorption band (or a portion of an absorption band) of the gas to be measured. The amount of radiation beam intensity absorbed by the gas will thus vary with wavelength, so converting the beam wavelength modulation into an amplitude modulation of the transmitted beam which has the same frequency as the wavelength modulation. The amplitude-modulated beam may then be measured by a radiation detector connected to, for example, a lock-in amplifier or a similar means of demodulating the signal.

In an alternative mode of operation of the present invention, the wavelength modulation can be set to occur symmetrically across the chosen absorption band (or a suitable portion of the chosen absorption band), about the band centre. In this case, an amplitude modulation will occur which has twice the frequency of the wavelength modulation. This alternative method of detection may not in general be so convenient as the preferred edge detection modulation because a larger wavelength modulation amplitude will be required to cover a complete absorption band (or a portion of the band) than to cover just one edge of the band, thereby increasing the possibility of interference by other gases.

If desired, the means for providing the radiation source means, the modulation means, the radiation detector means, and the amplitude modulation means may be formed as a single unit. A radiation beam can be sent out to a retro-reflector, such for example as a cube corner mirror, set at a suitable distance from the single unit, and the retro-reflector can then return the radiation beam to the radiation detector means.

The purpose of the two different modulations is to generate two separate signals at the radiation detector means. One of these, the wavelength modulation one, is dependent upon the presence of the gas being monitored while both are dependent, in a similar fashion, upon the total intensity of the radiation that reaches the radiation detector means. Ratioing the two signals against one another produces a gas measuring signal which depends upon the amount of gas being monitored but is independent of factors that reduce the intensity of the returned beam, such as beam divergence and absorption or scattering by atmospheric phenomena such as rain or refractive index fluctuations.

The wavelength modulation means may be an interference filter. The amplitude modulation means may be a rotating chopper device, a liquid crystal modulator or other device.

Typically, the rotating chopper device is a rotating disc with cut outs to allow the intermittent passage of the radiation beam.

In an alternative embodiment of the invention, the amplitude modulation means may be a switch device for switching the means for providing the radiation beam on and off at the required frequency.

In further alternative embodiments of the invention, the wavelength modulation means may be a prism, a diffraction grating or a Fabry-Perot etalon.

Usually, the optical gas monitoring apparatus will be one in which the means for providing the radiation beam is a direct source of radiation. If desired, the means for providing the radiation beam may be an image of a direct source of radiation. The direct source of radiation is typically an incandescent lamp but other direct sources of radiation may be employed if desired, such as light-emitting diodes.

The apparatus of the invention may include output/collection optics. The output/collection optics may be a Newtonian telescope or a Cassegrain or other arrangement.

The apparatus of the invention may operate over a path which can be from 3 meters to more than 400 meters long.

The optical gas monitoring apparatus of the present invention may provide the following advantages.

1. A single detector system having none of the signal drift problems that can occur in twin-detector systems.

2. Good gas detection sensitivity, due to the use of the wavelength modulation.

3. A simple and compact optical system, giving ease of construction and optical alignment.

4. Good signal stability which does not depend on the subtraction of two large signals, as is required for differential gas absorption and gas correlation.

5. A change of target gas can be effected with a change of a single filter, or in some cases just with a change of filter angle.

6. Good discrimination against other gases, through optimisation of the filter's wavelength, bandwidth and modulation amplitude, plus a choice of first or second harmonic detection as will be described in more detail hereinbelow.

7. Changes of sensitivity towards a gas can be produced by a change in filter angle, moving the operational wavelength into a weaker or stronger portion of the target gas absorption band as desired.

8. Simple spectroscopy is possible as an aid to gas identification, by steadily varying the filter angle.

Embodiments of the invention will now be described solely by way of example and with reference to the accompanying drawings in which:

FIG. 2 illustrates the optical portion only of a basic wavelength-modulated optical long-path gas monitoring apparatus;

FIG. 3 shows chromatic image formation by an inclined interference filter and lenses;

Figure 1:
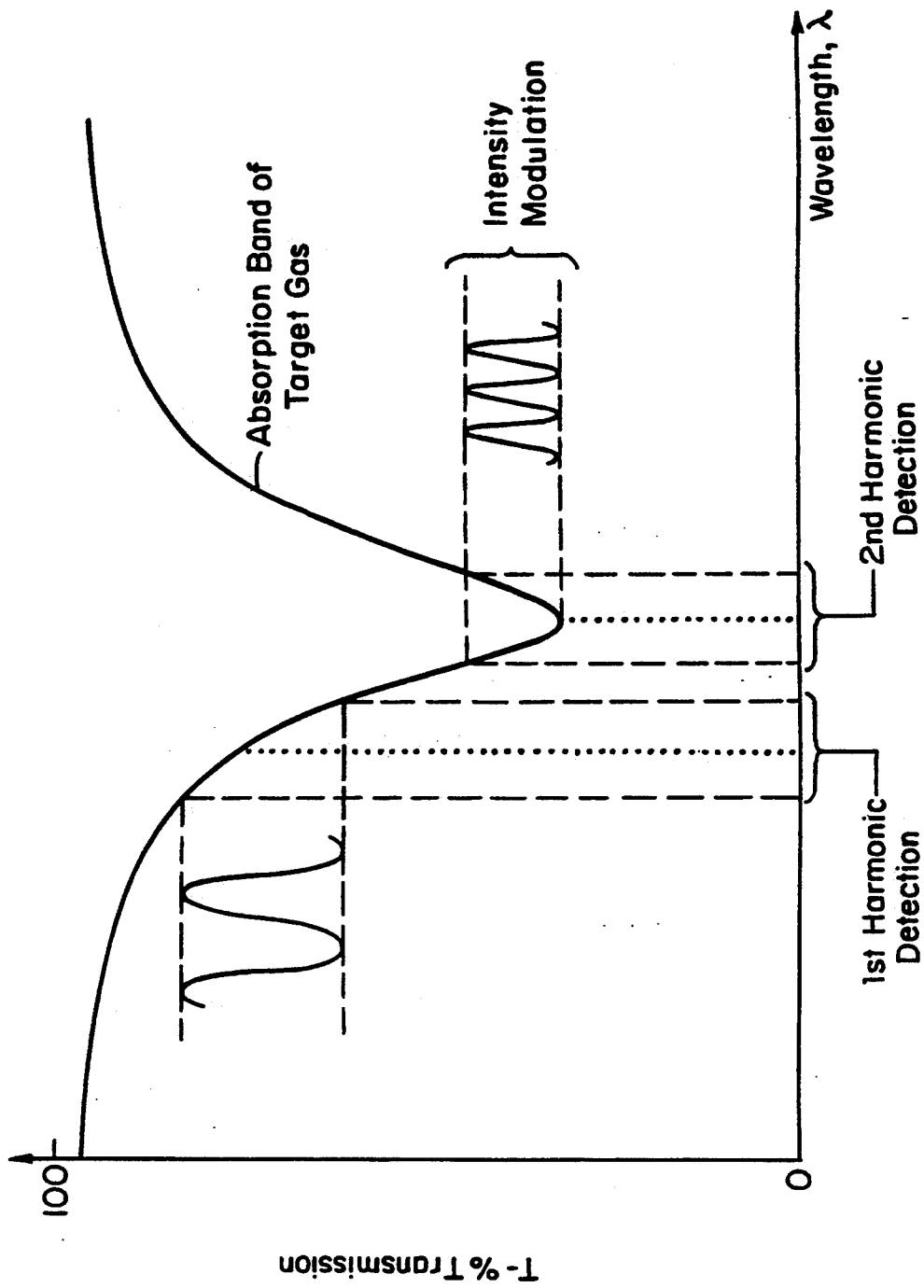
FIG. 1 illustrates the modulation effected during open path gas measurement wavelength modulation by two different means.

Referring to FIG. 1, the optical gas monitoring apparatus of the present invention operates on the principle of wavelength modulation and a single beam of radiation is employed which is continuously modulated in wavelength. This is used to detect the gas by setting the wavelength to modulate across an edge of an absorption band, or a portion of an absorption band, of the gas to be monitored. The amount of beam intensity absorbed by the gas will thus vary with wavelength, so converting the beam wavelength modulation into an amplitude modulation of the transmitted beam which has the same frequency as that of the wavelength modulation. This is referred to in FIG. 1 as "first harmonic detection". The amplitude modulation is then measured by a lock-in amplifier (not shown in FIG. 1).

In an alternative mode of operation, the wavelength modulation can be set to occur symmetrically across the chosen absorption band, or a suitable portion of that band, about the band center. In this case, an amplitude modulation will occur which has twice the frequency of the wavelength modulation. This is shown in FIG. 1 as "second harmonic detection". With second harmonic detection, a larger wavelength modulation amplitude will generally be required to cover the complete absorption band, or portion of an absorption band, of the gas being detected, thereby increasing the probability of interference by other gases. Thus the mode of operation using the first harmonic detection will often be preferred. There may however be cases where the second harmonic detection will be preferred. If desired, third or higher harmonic detection of the modulation frequencies is possible, but this will generally require even larger modulations.

An advantage of using wavelength modulation is that the gas detection signal is in principle generated only when the gas to be monitored is present, and the gas detection is not derived, as in differential absorption systems, from a comparison of two large signals which may drift in relative size with time. In this connection however, it is to be mentioned that in practice there is also a background signal in the absence of any gas. This is because the whole system is sensitive to changes of beam intensity with wavelength, and both the output of the radiation source and the sensitivity of the radiation detector will themselves vary somewhat with wavelength. The transmission efficiencies of the filters will also vary with filter angle and hence with the transmission wavelength. This background signal will be constant at any one chosen operational wavelength, and so, in practice, it will be subtracted from the total instrument signal, for example by electronic or digital means, in order to obtain the true gas signal.

In the illustrated apparatus of the present invention, a total power signal may be generated, via direct beam amplitude modulation at a radiation source using a chopper. By ratioing the wavelength modulation signal against the total power signal, the gas concentration can be measured, while removing fluctuations in atmospheric transmission.

Referring now to FIG. 2, there is shown optical gas monitoring apparatus 2, comprising means in the form of a radiation source 4 for providing a radiation beam. As an alternative to the radiation source 4, the means for providing the radiation beam may be an image of the radiation source. The apparatus 2 further comprises a pair of lenses 6, 8, modulation means in the form of a filter 10, and radiation detector means 12. The filter 10 is for modulating the wavelength of the radiation beam. The radiation detector means 12 is for detecting the intensity of the radiation beam, which is modulated consequent upon the presence of a gas being monitored.

The apparatus shown in FIG. 2 may be produced at relatively low cost. The infrared source 4 can be a simple incandescent lamp and the filter 10 can be an interference filter that is oscillated about an axis in its own plane by, for example, a commercially available galvanometer-type scanner. In alternative designs, the interference filter 10 may be replaced by a prism, a diffraction grating or a Fabry-Perot etalon, while the lenses may be replaced by concave mirrors.

Referring to the filter 10, the transmission band of bandpass interference filters is known to shift to shorter wavelengths as the filters are rotated away from their normal incidence positions so that oscillation of the filter 10 in front of a broad band source produces a transmitted optical beam that repetitively sweeps in wavelength. For example, in the near infrared region a wavelength shift of at least 600 $cm^{-1}$ can be produced for a 60° rotation of the filter 10 from normal incidence. This may be compared, for example, with a typical width of around 300 $cm^{-1}$ for the main absorption band of many common flammable hydrocarbon gases in this spectral region. In the mid infrared region, filter shifts tend to be smaller, as measured in wavenumbers, but so also are the widths of typical gas absorption bands.

As can be seen from FIG. 2, the apparatus 2 is such that the oscillating filter 10 is mounted between the two lenses 6, 8 such that the radiation beam passes through the angled filter 10 in an essentially parallel beam. The filter 10 is chosen such that it transmits in a wavelength region where the absorption of the gas to be monitored is varying strongly with the wavelength (see FIG. 1). The radiation source 4 is placed at or near the focus of the lens 6. The radiation detector means 12 is placed at or near the focus of the lens 8. The gas to be monitored can be introduced at any point along the optical path. The radiation detector means 12 is attached to the signal processing means which may incorporate one or more lock-in amplifiers. The lock-in amplifiers may be phase sensitive detectors. A lock-in amplifier is locked to the oscillation frequency of the filter since, if the gas to be detected is present, the lock-in amplifier will detect an amplitude modulation of the transmitted beam at this frequency (see the first harmonic detection in FIG. 1) or at twice this frequency in the case of the second harmonic detection (also see FIG. 1).

The optical gas monitoring apparatus operates over a long path and it is convenient to keep the radiation source 4 and the detector means 12 close together in a single unit, and to send the light beam out to a suitable retro-reflector such for example as a cube-corner mirror. The retro-reflector can be set at a suitable distance from the unit and the retro-reflector will then return the light beam to the detector means. The oscillating filter 10 can be placed in front of either the radiation source 4 or the radiation detector means 12. For a very short optical path system, these positions are essentially equivalent but for a long path system the positions have different features. The advantage of placing the filter 10 in front of the radiation source 4 is that if any local stray radiation manages to traverse the filter 10, virtually none of this local stray radiation is likely to be able to traverse the long and well defined optical path to the radiation detector means 12. Thus no false signals should occur. However, with the filter 10 in front of the radiation source 4, a chromatic image of the source is formed in the far field as shown in FIG. 3. In FIG. 3, which is deliberately exaggerated, it can be seen that the rays forming the image A' at the point A on the source A-B have passed through the filter 10 parallel to one another and at an angle $\alpha$ to the filter 10, whereas those forming the image B' of the point B on the source A-B are likewise parallel to each other at the filter 10 but strike it at a different angle $\beta$. Since the wavelengths transmitted by the filter 10 change with filter angle, the wavelength of rays arriving at B' will be somewhat different from those arriving at A'. In general, the retro-reflector 14 positioned at the far end of the optical path will be smaller than the image diameter A' B'. Thus any significant movement of the radiation beam across the retro-reflector 14, due to refractive index changes in the air or to mechanical movement of the beam output optics, will cause a wavelength change and hence a spurious signal. Such geometry-dependent signals would be particularly inconvenient if the optical gas monitoring apparatus were being used over a series of different paths in succession, such as in a portable mode of operation, or when moving regularly between different retro-reflectors 14 to routinely monitor, for example, a chemical storage plant.

The alternative method of placing the filter 10 near the radiation detector means 12 removes the above mentioned chromatic image problem because the far field image is then achromatic. The only chromatic image produced is the one formed on the radiation detector means 12 itself, and this can be arranged to underfill the detector element so that all the wavelengths present contribute to the detector signal regardless of any spatial separations that may have been introduced. However, this configuration introduces the difficulty that local stray radiation, from sources either inside or outside the apparatus, may also be able to pass through the filter 10 and reach the radiation detector means 12 since the optical path between the filter 10 and the radiation detector means 12 is so short. Such stray radiation will be wavelength modulated along with radiation that has traversed the long path, and so again a spurious signal will result. This problem may be overcome by the use of an electronic switch controlled by a beam chopper. The optical layout and a simplified block diagram of the electronics for this technique are shown in FIG. 4.

Figure 4:
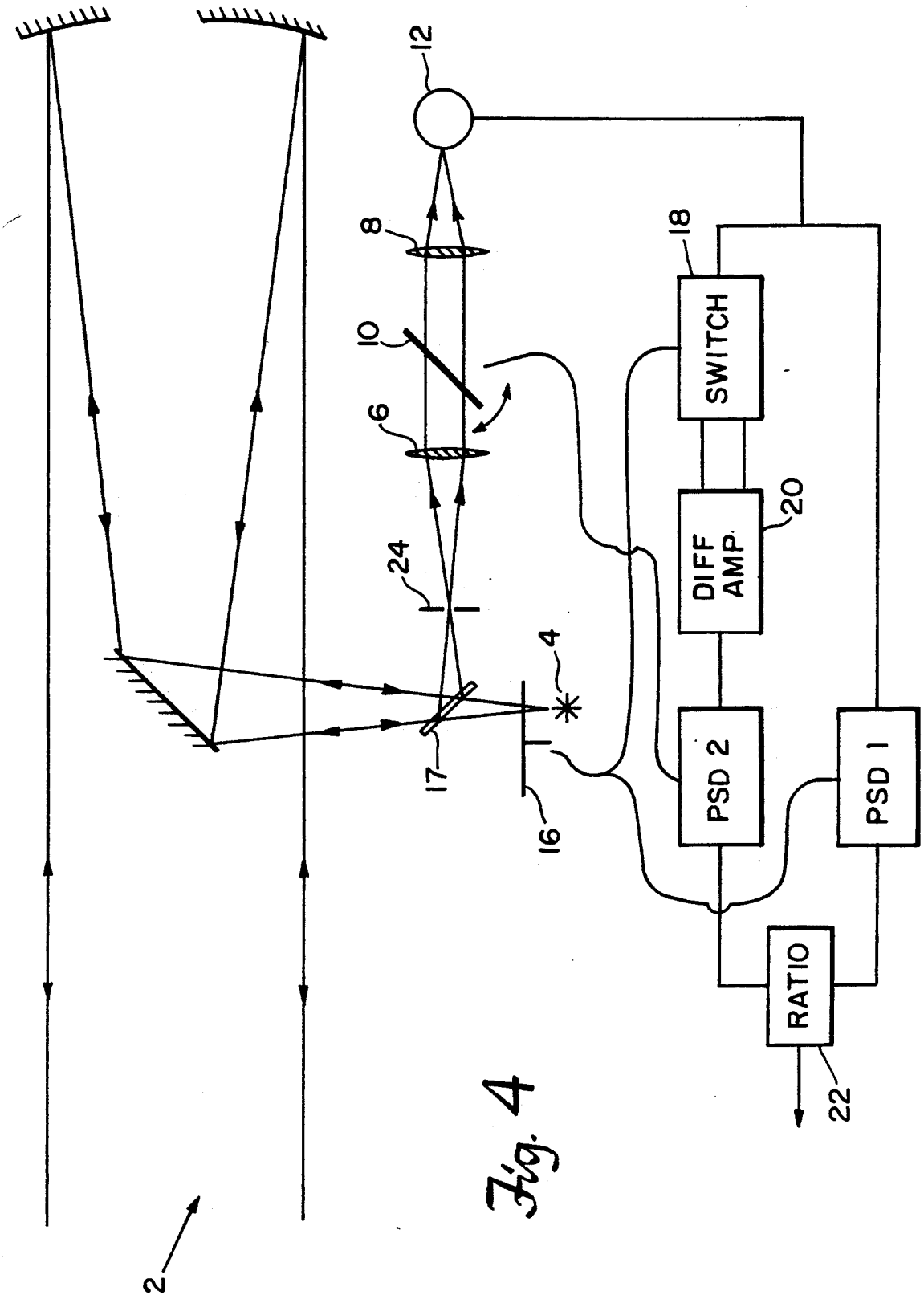
FIG. 4 shows optical long-path gas monitoring apparatus with a wavelength modulation system with background suppression.

Referring now to FIG. 4, there is shown optical gas monitoring apparatus 2 comprising a beam chopper 16 situated immediately in front of the radiation source 4. The beam chopper 16 has a dual function. The first function is to amplitude modulate the intensity of the beam that traverses the full long optical path and reaches the radiation detector means 12 via a beam splitter 17. This produces a detector signal at the amplitude modulation frequency which is measured by the phase sensitive detector PSD 1. The phase sensitive detector PSD 1 provides an output signal that is proportional to the total beam intensity returned to the radiation detector means 12.

The second function of the beam chopper 16 is to control an electronic switch 18 such that when the beam chopper 16 is open, the detector signal is directed to one input of an adjacent differential amplifier 20, and when closed is directed to the other input. The output of the differential amplifier 20 is fed to a second phase sensitive detector PSD 2. The second phase sensitive detector PSD 2 is set to detect modulation at the filter oscillation frequency. When the chopper 16 is open, the radiation detector means 12 sees radiation modulated at the filter frequency which comes both from the genuine long path beam and from any local stray radiation which has traversed the filter 10. When the chopper 16 is closed, only the stray radiation is seen. Thus subtraction of the "closed" from the "open" signal by the differential amplifier 20 produces an input to the phase sensitive detector PSD 2 which is due only to wavelength modulation radiation that has traversed the full long path and not due to stray background radiation.

The output from the phase sensitive detector PSD 2 is ratioed against the output from the phase sensitive detector PSD 1 to provide a ratio output signal that is approximately proportional to target gas concentration but independent of fluctuations in beam intensity and stray background intensity. The ratio output signal is shown diagramatically as ratio output signal 22.

A further advantage of the chopper-controlled switch is that it greatly reduces the relatively large amplitude modulation at the chopper frequency in the signal fed to the phase sensitive detector PSD 2 and so improves detection of the wavelength-modulated signal.

In FIG. 4, the signal processing means is essentially all of the electronics shown in FIG. 4, that is the PSD 1, the PSD 2, one differential amplifier and one electronic switch.

As indicated above, even with no gas present, the monitoring apparatus produces a background signal. However, if the monitoring apparatus is monitoring over a long atmospheric path, there well may be some of the "target" gas present in the path. This will give rise to a genuine gas signal, but it will not be clear how much of the total signal is genuine and how much is background. However, this can be determined by temporarily placing another retroreflector very close to the monitoring apparatus, so reducing the path length to nearly zero. Any residual signal is then the background signal. This technique works well as long as the background signal is the same for both long and short paths, but this requirement was found not to be quite the case with the optical gas monitoring apparatus shown in FIG. 4.

Referring to FIG. 4, a simple modification is effective to provide the solution to the above mentioned problem. More specifically, a small aperture 24 is placed at the return focus of the optical beam. The aperture 24 is made of such a size that most of the optical beam can just pass through the aperture when the monitoring apparatus is being used over a fairly normal length, typically 100 meters from the monitoring apparatus to the retro-reflector. However, at very short path lengths, used to find the gas zero, only a small proportion of the radiation beam can pass through the aperture 24, since under these conditions the size of the return focus is much greater than the aperture 24. Thus, the dimensions of the beam passed through the aperture 24 and reaching the oscillating filter are fairly similar for all path lengths, and as a result the background signal is likewise found to be similar, as is required. Furthermore, there is also less difference in the total optical power received at the detector for long and short path lengths. Hence the range of signal strengths that have to be handled by the processing electronics is reduced, with consequent improvement in the accuracy of signal measurement.

Figure 5:
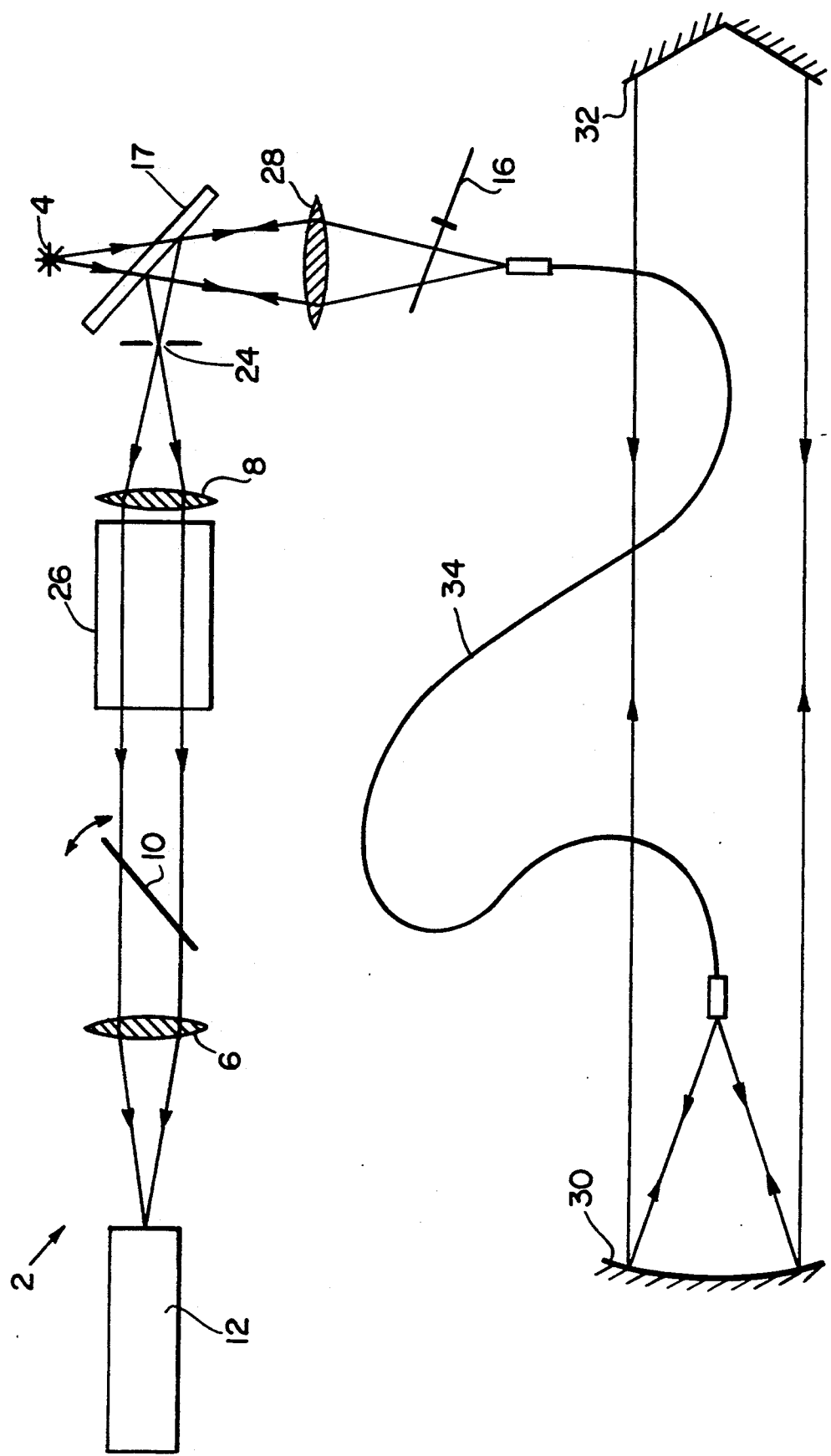
FIG. 5 shows fiber-link gas monitoring apparatus.

Referring now to FIG. 5, there is shown fiber-link gas monitoring apparatus 2. Similar parts as in previous Figures have been given the same reference numerals for ease of comparison and understanding. In the apparatus 2 shown in FIG. 5, it will be seen that there is additionally provided a gas cell 26, an objective lens 28, a concave mirror 30, a retro-reflector 32 and a fiber-optic cable 24.

As can be seen from FIG. 5, the fiber-optic cable 34 is placed between the telescope and the remainder of the apparatus 2. The illustrated arrangement has the potential advantage that if the apparatus 2 is being used in some flammable atmosphere, then only the telescope unit (which has no moving parts and no electrical supplies) need be in the hazardous area, whilst the remainder of the system can be in a safe area at the far end of the fiber-optic cable 34.

Figure 6:
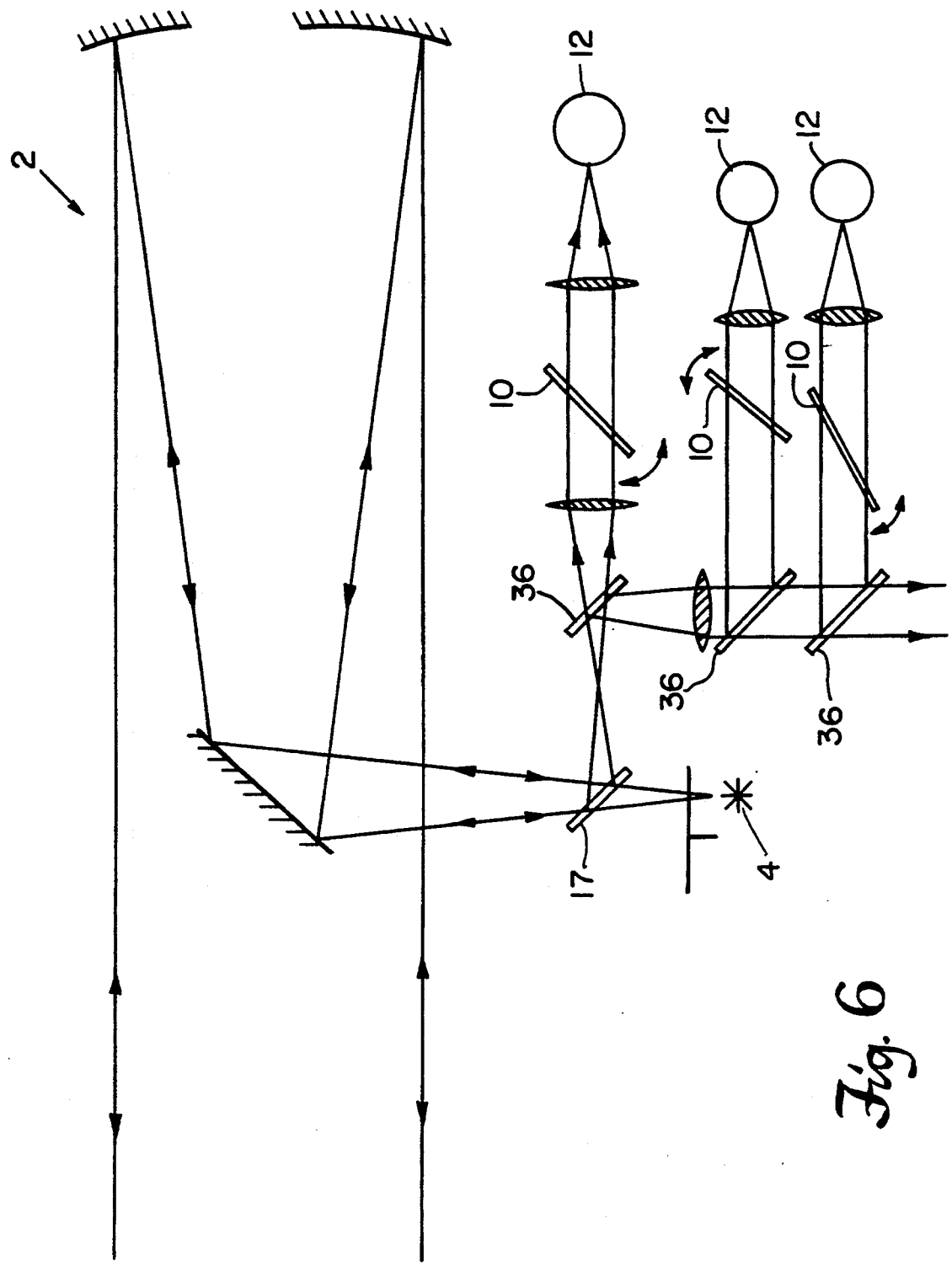
FIG. 6 shows gas monitoring apparatus for multiple gas sensing.

Referring now to FIG. 6, there is shown gas monitoring apparatus 2 which is for use for multiple gas sensing. Again, for ease of comparison and understanding, similar parts as in previous Figures have been given the same reference numerals. The configuration shown in FIG. 6 allows monitoring of several gases simultaneously. As shown, if use is made of one or more dichroic mirrors 36 (that is mirrors that reflect some wavelengths but that transmit other wavelengths) then the broad spectrum of wavelengths emitted by the incandescent lamp source 4 and transmitted through the atmosphere can be split up into a number of wavelength intervals. Each of the different intervals can then be used to measure a different gas, and all the measurements may be made simultaneously. A different detector, filter and electronics unit is of course needed for each gas and FIG. 6 shows a configuration for the measurement of three gases.

It is to be appreciated that the embodiments of the invention described above with reference to the accompanying drawings have been given by way of example only and that modifications may be effected.

As an alternative to employing a rotating disc with cut outs to allow the intermittent passage of the optical beam to modulate the radiation beam at a particular frequency, the radiation source 4 may itself be switched on and off at the required frequency. A suitable optical/electronic link would be required in order to operate the electronic switch.

The optical system illustrated in FIG. 4 may be varied so that, for example, the illustrated Newtonian telescope output/collection optics may be replaced by a Cassegrain or other arrangement. Also, the beam launch optics may be separated from the beam collection optics, and indeed these could be placed at the opposite ends of the measurement path instead of at the same end as shown in FIG. 4. Similarly, the lenses 6, 8 on either side of the oscillating filter 10 may be replaced by concave mirrors. The electronics may be varied as may be desired.

Although the embodiments of the invention described above with reference to the accompanying drawings have illustrated the use of an oscillating filter 10 as the wavelength modulating element, this has only been so because the oscillating filter 10 is relatively cheap. It is to be appreciated however that other wavelength dispersing elements may be employed in place of the filter 10 so that the filter 10 may be replaced by a prism, a diffraction grating or a cavity-modulated Fabry-Perot etalon. The prism and the diffraction grating would need direct or indirect angular oscillation, as for the filter 10. They would thus need to be placed next to the detector in the long path system in order to avoid the above mentioned chromatic image problems mentioned above, and they would thus require the stray light subtraction system mentioned above. With the cavity-modulated Fabry-Perot etalon, this is somewhat similar to the mode of operation of the filter 10 insofar as the interference filter is essentially a solid Fabry-Perot etalon. However, the air-space cavity-modulated Fabry-Perot etalon differs in that the spacing between the two etalon plates is varied (often by piezo-electric movement of one of the plates) so varying the transmitted wavelength. This means that the radiation beam can traverse the Fabry-Perot etalon at near normal incidence to the plates for all desired wavelengths, rather than at different angles for different wavelengths as for the filter 10. One practical consequence of this is that the Fabry-Perot etalon would produce less of a chromatic image at long distances than would the filter 10, the prism or the diffraction grating. Thus, in some systems, it may be possible to place the Fabry-Perot etalon near the radiation source 4 rather than the radiation detector means 12, so removing the requirement for stray radiation subtraction via an electronic switch.

We claim:

1. Optical long-path gas monitoring apparatus comprising radiation source means for providing a radiation beam having a broad range of wavelengths, wavelength modulation means for modulating the radiation beam at a wavelength modulation frequency over all of the wavelengths between two limits appropriate for the gas being monitored in order to produce amplitude modulation of the radiation beam in the presence of the gas being monitored, amplitude modulation means for modulating the radiation beam at a frequency different from that of the wavelength modulation frequency, radiation detector means for converting the radiation into an electrical signal, and signal processing means comprising two phase sensitive detectors to demodulate the amplitude modulated and phase modulated signals respectively to provide, upon ratioing the outputs of the phase sensitive detectors, a signal dependent upon the gas being monitored, the optical long-path gas monitoring apparatus being such that the amplitude modulation means is positioned in front of the radiation source means and in the path of a radiation beam emitted from the radiation source means into the atmosphere, and the wavelength modulation means is positioned in front of the radiation detector means such that it will be traversed by the radiation beam after the radiation beam has traversed a selected portion of the atmosphere, and the optical long-path gas monitoring apparatus being such as to include an electronic switch which is controlled by the amplitude modulation means and whose purpose is to provide two different signals at times when the amplitude modulation means is open and closed respectively, which signals when subtracted one from the other remove spurious signals in the wavelength modulation channel due to external stray radiation.

2. Optical long-path gas monitoring apparatus according to claim 1 in which the radiation source means, the wavelength modulation means, the radiation detector means, and the amplitude modulation means are formed as a single unit.

3. Optical long-path gas monitoring apparatus according to claim 2 and including a telescope which is connected to the single unit.

4. Optical long-path gas monitoring apparatus according to claim 3 in which the telescope is connected to the single unit by a fibre-optic cable.

5. Optical long-path gas monitoring apparatus according to claim 2 and including a retro-reflector positioned remote from the single unit such that the means for providing the radiation beam can send the radiation beam to the retro-reflector, and the retro-reflector can then return the radiation beam to the radiation detector means.

6. Optical long-path gas monitoring apparatus according to claim 1 in which the wavelength modulation means is an interference filter, and in which the amplitude modulation means is selected from the group consisting of a rotating chopper device and an electro-optic modulator.

7. Optical long-path gas monitoring apparatus according to claim 1 in which the amplitude modulation means is a switch device for switching the means for providing the radiation beam on and off at the required frequency.

8. Optical long-path gas monitoring apparatus according to claim 1 in which the wavelength modulation means is selected from the group consisting of a prism, a diffraction grating, and a Fabry-Perot etalon, and in which the optical long-path gas monitoring apparatus includes output/collection optics.

9. Optical long-path gas monitoring apparatus according to claim 1 and including a small aperture at a return focus of the radiation beam, the small aperture being such as to limit the size of the transmitted portion of the radiation beam at the said return focus in order to reduce changes of background signal between long and short paths.

10. Optical long-path gas monitoring apparatus according to claim 1 and including at least one dichroic mirror for splitting up the radiation beam into at least two radiation beams, at least one further wavelength modulation means, and at least one further radiation detector means, the optical long-path gas monitoring apparatus then being for monitoring more than one gas.

* * * * *